United States Patent [19]

Yamamoto et al.

[11] 4,272,637
[45] Jun. 9, 1981

[54] CATALYST FOR OXIDATION OF ISOBUTYLENE

[75] Inventors: Haruhisa Yamamoto; Nobuaki Yoneyama; Shinichi Akiyama, all of Takaoka, Japan

[73] Assignee: Nippon Zeon Co., Ltd., Tokyo, Japan

[21] Appl. No.: 971,302

[22] Filed: Dec. 20, 1978

[30] Foreign Application Priority Data

Dec. 28, 1977 [JP] Japan .................. 52-159553

[51] Int. Cl.$^3$ .................. C07C 45/35; C07C 47/22
[52] U.S. Cl. .................. 568/780; 568/476; 252/437
[58] Field of Search .................. 260/604 R; 252/435, 252/437; 568/480, 476

[56] References Cited

U.S. PATENT DOCUMENTS

| 3,968,166 | 7/1976 | Shiraishi et al. | 562/546 |
| 4,035,418 | 7/1977 | Okada et al. | 562/546 |
| 4,148,757 | 4/1979 | Brazdil et al. | 562/546 |

FOREIGN PATENT DOCUMENTS 48-17253  5/1973 Japan .................. 260/604

Primary Examiner—Werren B. Lone
Attorney, Agent, or Firm—Wenderoth, Lind & Ponack

[57] ABSTRACT

A catalyst for oxidation of isobutylene which has a composition of the general formula $$Mo_aBi_bFe_cCo_dNi_eP_fPb_gX_hO_i$$

wherein X is at least one alkali metal element selected from K, Rb and Cs; a, b, c, d, e, f, g and h respectively represent the number of Mo, Bi, Fe, Co, Ni, P, Pb and X atoms, and when a is 12, b is 0.1–10, c is 9–20, d is 0–12, e is 0–12 with the proviso that the sum of d and e is 0.5–15, f is 0.1–5, g is 0.05–8 and h is 0.01–5; and i is the number of oxygen atoms which satisfies the atomic valences of the other elements.

8 Claims, No Drawings

CATALYST FOR OXIDATION OF ISOBUTYLENE

This invention relates to a catalyst for oxidation of isobutylene, and a process for producing methacrolein by oxidizing isobutylene in the presence of the aforesaid catalyst.

Some of the terms used in the present application are defined as follows:

The "first-stage oxidation" denotes the catalytic vapor-phase reaction of isobutylene with molecular oxygen at high temperatures in the presence of a catalyst to form methacrolein.

The "second-stage oxidation" denotes the catalytic vapor-phase reaction of methacrolein with molecular oxygen at high temperatures in the presence of a catalyst to form methacrylic acid.

The "continuous first stage-second stage method" denotes a method for producing methacrylic acid from isobutylene by feeding the gaseous reaction mixture formed in the first-stage oxidation directly to a second-stage oxidation zone to perform the second-stage oxidation.

The "catalyst for oxidation of isobutylene", or the "catalyst for the first-stage oxidation" denotes a catalyst which is used in the first-stage oxidation.

The "catalyst for the second-stage oxidation" denotes a catalyst which is used in the second-stage oxidation.

It is known to produce methacrolein by oxidizing isobutylene, and to produce methacrylic acid by oxidizing methacrolein. Known prior techniques for the production of methacrylic acid from isobutylene include a method which comprises separating methacrolein from the reaction mixture obtained by the first-stage oxidation, and after purifying it, submitting it to a second-stage oxidation, and a method which involves performing the first-stage oxidation and the second-stage oxidation successively without working up the first-stage reaction mixture (British Pat. No. 939,713). The latter is considered to be commercially advantageous because it does not require a treating step such as the separation and purification of methacrolein, and therefore is advantageous in apparatus, operation and economy.

However, the continuous first stage-second stage method generally gives far inferior results compared to the case of independently performing the second-stage oxidation using the purified methacrolein as a starting material. For this reason, no suggestion has been made so far which would make possible the commercial production of methacrylic acid by the continuous first stage-second stage method.

The underlying difficulties are believed to be the formation of by-product impurities and the remaining of unreacted isobutylene in the first-stage oxidation. The present inventors carefully studied these difficulties, and found that the reaction mixture obtained by the first-stage oxidation contains, as by-products, unsaturated hydrocarbons such as diisobutylene, benzene, toluene, xylene and ethylbenzene in addition to the unreacted isobutylene, and the presence of these hydrocarbons is a main cause for the inferior reaction results in the second-stage oxidation.

In the production of methacrylic acid from isobutylene by the continuous first stage-second stage method, it is desired to develop a novel oxidation catalyst that simultaneously meets the following two requirements which seem to be inconsistent with each other.

(1) It should afford a high conversion of isobutylene and thus reduce the amount of the unreacted isobutylene.

(2) It should reduce the formation of unsaturated hydrocarbons such as diisobutylene, benzene, toluene, xylene and ethylbenzene.

In addition to these requirements, such a catalyst should also meet normal requirements for industrial catalysts such as a high selectivity to MAL (which is associated with a high one-pass yield), and a long active lifetime.

Accordingly, it is an object of this invention to provide a novel catalyst for oxidation of isobutylene, which can afford methacrolein from isobutylene in a high selectivity and a high one-pass yield, and has a long active lifetime.

Another object of this invention is to provide a novel catalyst for oxidation of isobutylene which meets the two requirements described above.

Still another object of this invention is to provide a process for preparing methacrolein in a high selectivity and a high yield by using such a catalyst for oxidation of isobutylene.

According to this invention, there is provided a catalyst which can achieve these objects, said catalyst having the composition $$Mo_aBi_bFe_cCo_dNi_eP_fPb_gX_hO_i$$

wherein X is at least one alkali metal element selected from K, Rb and Cs; a, b, c, d, e, f, g and h respectively represent the number of Mo, Bi, Fe, Co, Ni, P, Pb and X atoms, and when a is 12, b is 0.1–10, c is 9–20, d is 0–12, e is 0–12 with the proviso that the sum of d and e is 0.5–15, f is 0.1–5, g is 0.05–8 and h is 0.01–5; and i is the number of oxygen atoms which satisfies the atomic valences of the other elements.

A catalyst of the above general formula in which when a is 12, b is 0.5–7, c is 10–15, d is 0–10, e is 0–10 with the proviso that the sum of d and e is 0.5–12, f is 0.1–4, g is 0.1–4 and h is 0.01–4 is a preferred embodiment of the present invention.

Although the exact structure of the catalyst of this invention is not clear, the composition of the ingredients forming the catalyst is believed to be basically expressed by the above general formula.

The use of these catalysts of the invention can afford methacrolein in a high yield and a high selectivity even when the conversion of isobutylene in its oxidation is high, and can drastically reduce the amounts of by-product unsaturated hydrocarbons such as diisobutylene, benzene, toluene, xylene or ethylbenzene. Accordingly, the catalysts of this invention are very suitable for production of methacrolein, and when used as a first-stage oxidation catalyst in the continuous first stage-second stage method, they do not substantially hamper the second-stage oxidation reaction over long periods of time.

Such an effect of this invention can be specifically obtained by the inclusion of Pb in the catalyst ingredients as shown in the above general formula. If this ingredient is not present, the activities of the catalysts are low, and the formation of by-product unsaturated hydrocarbons greatly increases.

Known catalysts having a composition similar to that of the catalysts of this invention show good performance only when the number of Fe atoms is within a range of 0.5 to 7 with the number of Mo atoms taken as 12 (for example, Japanese Patent Publication No. 17253/73). In contrast, the catalysts of this invention exhibit a high activity when the number of Fe atoms is within a range of 9 to 20.

The catalysts of this invention can be prepared by various methods known in the art such as an evaporation method, an oxide mixing method and a coprecipitation method. The starting materials for the individual elements in the catalyst may be not only their oxides, but any other compounds which will constitute the catalyst of this invention by calcination. Examples of these starting materials are salts containing these elements (such as ammonium salts, nitrate salts, carbonate salts, organic acid salts, and halides), free acids, acid anhydrides, condensed acids, and heteropolyacids containing molybdenum such as phosphomolybdic acid or silicomolybdic acid, and their salts such as ammonium salts or metal salts The use of a silicon-containing compound such as silicomolybdic acid does not adversely affect the activity of the resulting catalyst.

Calcination treatment for the purpose of catalyst preparation, catalyst activation, etc. is performed usually at 300° to 900° C., preferably 450° to 700° C. for about 4 to 16 hours. If desired, a primary calcination treatment may be performed at a temperature below the above-mentioned calcination temperature before the above calcination treatment.

The catalysts of this invention can be used directly as prepared, and also as deposited on a carrier of a suitable shape, or as diluted with a carrier (diluent) in the form of powder, sol, gel, etc. Known carriers can be used for this purpose. Examples include titanium dioxide, silica gel, silica sol, diatomaceous earth, silicon carbide, alumina, pumice, silica-alumina, bentonite, zirconia, zeolite, and refractories. Silicon-containing carriers are especially suitable.

The amount of the carrier can be suitably chosen. The catalyst is made into a suitable shape such as powder or tablets, and can be used in any of a fixed bed, a moving bed, and a fluidized bed.

Isobutylene used in the reaction need not always be of high purity, and may contain impurities. However, when the oxidation is performed by the continuous first stage-second stage method, the inclusion of large amounts of n-butene, butadiene and the like impurities is undesirable because it will possibly result in the inclusion of unsaturated hydrocarbons in the reaction gas obtained in the first-stage oxidation. Molecular oxygen may be singly used, but for commercial operations, the use of air is practical. Furthermore, in this reaction, the molecular oxygen may be diluted with an inert gas which does not adversely affect the reaction, such as steam, nitrogen, argon or carbon dioxide gas. It is especially preferred to dilute it with steam.

In the production of methacrolein from the corresponding isobutylene using the catalysts of this invention, the reaction temperature is 250° to 700° C., preferably 250° to 550° C.; the reaction pressure is normal atmospheric pressure to 10 atmospheres; the space velocity (SV) of the entire starting gases is 200 to 10000 $hr^{-1}$, preferably 300 to 6000 $hr^{-1}$ (based on STP); isobutylene concentration in the fed starting gases is 0.5 to 25% by volume; and the isobutylene to oxygen ratio is 1:0.5–7. The preferred composition of the starting gaseous mixture is olefin:air:steam = 1:3–30:5–90 (molar ratio).

The reaction conditions in the first-stage oxidation in the continuous first stage-second stage method can be easily determined experimentally if a catalyst for the second-stage oxidation is set. Hence, the reaction conditions for the first-stage oxidation cannot be definitely fixed. Usually, however, the reaction temperature is 250° to 700° C., preferably 250° to 550° C.; the reaction pressure is normal atmospheric pressure to 10 atmospheres; the space velocity of the entire starting gases is 200 to 10000 $hr^{-1}$, preferably 300 to 4000 $hr^{-1}$; the isobutylene concentration is 0.5 to 10% by volume, preferably 0.5 to 8% by volume; the isobutylene to oxygen ratio is 1:1.5–7; and the preferred composition of the gaseous mixture is isobutylene:air:steam = 1:7.5–30:5–90 (molar ratio).

For the second-stage oxidation in the continuous first stage-second stage method, any known catalysts can be used. Examples include (1) P-Mo-R (R is at least one of Tl, alkali metals and alkaline earth metals) type oxidation catalysts; oxidation catalysts having compositions resulting from incorporating the above P-Mo-R type oxidation catalysts with at least one element selected from Si, Cr, Al, Ge, Ti, V, W, Bi, Nb, B, Ga, Pb, Sn, Co, Pd, As, Zr, Sb, Te, Fe, Ni, In, Cu, Ag, Mn, La, Nb, Ta and Sm; (2) P-Mo-As type oxidation catalysts; (3) P-Mo-As-alkali metal type oxidation catalysts; oxidation catalysts having compositions resulting from the incorporation of the P-Mo-As-alkali metal type catalysts with at least one element selected from V, W, Cu, Fe, Mn and Sn; (4) P-Mo-Sb type oxidatiaon catalysts, oxidation catalysts having compositions resulting from the incorporation of the P-Mo-Sb type catalysts with at least one element selected from W, Fe, Co, V, Al, Pb, Cr, Sn, Bi, Cu, Ni, Mg, Ca, Ba and Zn; (5) P-Mo-Pd type oxidation catalysts; (6) P-Pd-Sb type oxidation catalysts; oxidation catalysts having compositions resulting from the incorporation of the P-Pd-Sb type catalysts with at least one element selected from Bi, Pb, Cr, Fe, Ni, Co, Mn, Sn, U and Ba; and oxidation catalysts having compositions resulting from the incorporation of the aforementioned oxidation catalysts with ammonium.

Among these, the catalysts of type (1) are desirable as second-stage oxidation catalysts because they exhibit very high activity. However, when methacrylic acid is to be produced by the continuous first stage-second stage method, they tend to decrease in activity owing to the presence of unsaturated hydrocarbons in the reaction mixture obtained by the oxidation of isobutylene, and this tendency is more outstanding than the other second-stage catalysts. However, when the catalyst in accordance with this invention is used in the first-stage oxidation, the production of by-product unsaturated hydrocarbons in the first-stage oxidation step is markedly inhibited, and therefore, the decrease in activity of the catalysts (1) can be prevented. As a result, the inherent activity of these catalysts can be maintained for long periods of time. Catalysts of this type are disclosed in detail, for example, in Japanese Patent Publications Nos. 19774/72, 24288/75, 10845/75, 10846/75, 15011/76, and 31327/77, and Japanese Laid-Open Patent Publications Nos. 82013/75, 123619/75, 83321/75, 83322/75, 84517/75, 84518/75, 84519/75, 84520/75, and 123616/75.

The second-stage oxidation is performed under substantially the same reaction conditions as in the first-stage oxidation, but as described above, specific conditions are selected according to the catalyst used. Preferably, the first-stage reaction mixture obtained under the aforesaid reaction conditions is directly offered as a starting material in the second-stage oxidation, and reacted under conditions suitable for the catalyst used.

The following examples specifically illustrate the present invention. In these examples, the conversion, selectivity and one-pass yield are calculated in accordance with the following equations. All analyses were made by gas chromatography. For simplicity, the indication of oxygen in the catalyst composition is omitted.

In the following description, i-B stands for isobutylene, MAL for methacrolein; and MAA for methacrylic acid.

[Calculating equations for the results of the first-stage oxidation]

$$\text{i-B conversion (\%)} = \frac{\text{Reacted i-B (moles)}}{\text{Fed i-B (moles)}} \times 100$$

$$\begin{aligned}\text{Percentage of unsaturated hydrocarbons} = &\frac{\text{Unreacted i-B (moles)}}{\text{Fed i-B (moles)}} + \\ &\frac{\text{Formed diisobutylene (based on carbon)}}{\text{Fed i-B (based on carbon)}} + \\ &\frac{\text{Formed benzene (based on carbon)}}{\text{Fed i-B (based on carbon)}} + \\ &\frac{\text{Formed toluene (based on carbon)}}{\text{Fed i-B (based on carbon)}} + \\ &\frac{\text{Formed xylene (based on carbon)}}{\text{Fed i-B (based on carbon)}} + \\ &\frac{\text{Formed ethylbenzene (based on carbon)}}{\text{Fed i-B (based on carbon)}} \times 100\end{aligned}$$

$$\text{One-pass yield of MAL (\%)} = \frac{\text{Formed MAL (moles)}}{\text{Fed i-B (moles)}} \times 100$$

$$\text{Selectivity of MAL (\%)} = \frac{\text{Formed MAL (moles)}}{\text{Reacted i-B (moles)}} \times 100$$

[Calculating equations for the results of the second-stage oxidation]

$$\text{MAL conversion (\%)} = \frac{\text{Reacted MAL (moles)}}{\text{Fed MAL (moles)}} \times 100$$

$$\text{One-pass yield of MAA (based on MAL) (\%)} = \frac{\text{Formed MAA (moles)}}{\text{Fed MAL (moles)}} \times 100$$

$$\text{Selectivity of MAA (based on MAL)(\%)} = \frac{\text{Formed MAA (moles)}}{\text{Reacted MAL (moles)}} \times 100$$

$$\text{Conversion of unsaturated hydrocarbons (\%)} = \frac{\text{Reacted unsaturated hydrocarbons (based on carbon)}}{\text{Fed unsaturated hydrocarbons (based on carbon)}} \times 100$$

$$\text{One-pass yield of MAA (based on i-B) (\%)} = \frac{\text{Formed MAA (moles)}}{\text{i-B fed to the first-stage oxidation zone (moles)}} \times 100$$

EXAMPLES 1 to 10

Bismuth nitrate (48.5 g), 116.5 g of cobalt nitrate, 29.1 g of nickel nitrate, 484.8 g of ferric nitrate, 33.1 g of lead nitrate and 10.1 g of potassium nitrate were added to 150 ml of water and dissolved by heating to form a solution (solution A). Separately, 212 g of ammonium molybdate was dissolved in 400 ml of water by heating, and 5.76 g of 85% phosphoric acid was added to form a solution (solution B).

Solution B was mixed with solution A which was stirred at an elevated temperature. With thorough stirring, the mixture was evaporated to dryness, and then dried at 120° C. for 8 hours. The dried product was calcined at 600° C. for 16 hours in a muffle furnace. The solid obtained was pulverized to form particles having a size of 4 to 8 mesh.

The composition of the catalyst of the invention so prepared was $Mo_{12}Bi_1Fe_{12}Co_4Ni_1Pb_1P_{0.5}K_1$.

By the same procedure as above, various catalysts having different compositions as shown in Table 1 were prepared.

Using these catalysts as first-stage oxidation catalysts, a continuous first stage-second stage reaction was performed by the following procedure.

(1) First-stage oxidation reaction 100 ml of the catalyst obtained was filled into a stainless steel reaction tube having an inside diameter of 2.5 cm and a length of 60 cm, and heated over a metal bath. A starting gaseous mixture of isobutylene, air and steam in a mole ratio of 4:55:41 was passed through the catalyst layer at a space velocity of 2000 $hr^{-1}$.

(2) Second-stage oxidation reaction

As a catalyst for the second-stage oxidation, 100 ml of the Mo-P-Cs-Cr catalyst disclosed in Example 1 of the specification of Japanese Patent Publication No. 10846/75 [Mo:P:Cs:Cr=1:0.16:0.16:0.16 (atomic ratio); calcined at 450° C.; catalyst particle diameter 4-8 mesh] was filled into a stainless steel reaction tube having an inside diameter of 2.5 cm and a length of 60 cm, and heated over a metal bath. The reacted gas obtained by the first-stage oxidatiaon was directly passed through the catalyst layer.

The results obtained in the first-stage oxidation and the second-stage oxidation are shown in Table 1. In Table 1, the reaction temperatures refer to those of the metal bath which were maintained constant (the same will apply hereinbelow).

For comparison, a catalyst not containing Pb (Example 8) and the catalyst (Example 9) described in Example 1 of Japanese Patent Publication No. 17253/73 were prepared (catalyst particle diameter 4-8 mesh), and their performances were rated in the same manner.

As a control, a gaseous mixture of methacrolein (purity 99.5% by weight):$O_2$:$N_2$:$H_2O$=1:1.5:13.0:17.5 (mole ratio) was fed at a space velocity of 2000 $hr^{-1}$ through the second-stage oxidation catalyst, and the results are also shown in Table 1 (Example 10).

TABLE 1

| | Results of the first-stage oxidation | | | | | | | | | | | | | |
|---|---|---|---|---|---|---|---|---|---|---|---|---|---|---|
| | Catalyst composition (atomic ratio) | | | | | | | | | Reaction temperature (°C.) | i-B conversion (%) | Proportion of unsaturated hydrocarbons formed (%) | MAL One-pass yield (%) | MAL Selectivity (%) |
| Example | Mo | Bi | Fe | Co | Ni | Pb | P | K | Rb | Cs | | | | | |
| Invention | | | | | | | | | | | | | | | |
| 1 | 12 | 1 | 12 | 4 | 1 | 1 | 0.5 | 1 | — | — | 340 | 98.4 | 2.7 | 76.4 | 77.6 |
| 2 | 12 | 3 | 15 | 4 | 1 | 0.5 | 0.5 | 1 | — | — | 345 | 98.1 | 2.9 | 76.2 | 77.7 |
| 3 | 12 | 1 | 10 | 4 | 1 | 3 | 1 | 1.5 | — | — | 350 | 97.5 | 3.4 | 75.8 | 77.7 |
| 4 | 12 | 1 | 12 | 4 | 1 | 0.1 | 0.5 | 0.75 | — | — | 330 | 98.0 | 2.7 | 77.0 | 78.6 |
| 5 | 12 | 1 | 12 | 6 | 1 | 1 | 3 | 2 | — | — | 355 | 97.4 | 3.2 | 76.5 | 78.5 |
| 6 | 12 | 1 | 12 | 4 | 1 | 1 | 0.5 | — | 0.5 | — | 340 | 98.2 | 2.8 | 77.0 | 78.4 |
| 7 | 12 | 1 | 12 | 4 | 1 | 1 | 0.5 | — | — | 0.2 | 345 | 97.9 | 2.9 | 75.1 | 76.7 |
| Comparison | | | | | | | | | | | | | | | |
| 8 | 12 | 1 | 12 | 4 | 1 | — | 0.5 | 1 | — | — | 340 | 95.5 | 7.3 | 69.4 | 72.7 |

TABLE 1-continued

| | | | | | | | | | | | | | | |
|---|---|---|---|---|---|---|---|---|---|---|---|---|---|---|
| 9 Control | 12 | 1 | 3 | 4.5 | 2.5 | — | 0.5 | 0.07 | — | — | 340 | 90.0 | 13.0 | 57.7 | 64.1 |
| 10 | — | — | — | — | — | — | — | — | — | — | — | — | — | — | — |

| | | | Results of the second-stage oxidation | | | |
|---|---|---|---|---|---|---|
| | Reaction | MAL con- | MAA (based on MAL) | | Conversion of unsaturated | One-pass yield of MAA |
| Example | temperature (°C.) | version (%) | One-pass yield (%) | Selectivity (%) | hydrocarbons (%) | (based on i-B) (%) |
| Invention 1 | 335 | 78.9 | 60.8 | 77.1 | 100 | 46.5 |
| 2 | 335 | 78.6 | 60.0 | 76.3 | 100 | 45.7 |
| 3 | 335 | 77.1 | 59.7 | 77.4 | 100 | 45.3 |
| 4 | 335 | 79.1 | 61.3 | 77.5 | 100 | 47.2 |
| 5 | 335 | 77.8 | 60.3 | 77.5 | 100 | 46.1 |
| 6 | 335 | 78.4 | 60.5 | 77.2 | 100 | 46.6 |
| 7 | 335 | 78.5 | 61.1 | 77.8 | 100 | 45.9 |
| Comparison 8 | 335 | 65.4 | 44.5 | 68.0 | 100 | 30.9 |
| 9 | 335 | 50.4 | 30.2 | 59.9 | 100 | 17.6 |
| Control 10 | 335 | 81.1 | 62.8 | 77.4 | — | — |

It is seen from the results shown in Table 1 that the use of the catalysts of this invention gives good reaction results in the first-stage oxidation, and also as good results in the second-stage oxidation reaction as are comparable to the case of using purified methacrolein. On the other hand, the catalyst not containing Pb gives poor results both in the first-stage oxidation reaction and in the second-stage oxidation reaction. It is also clear from the table that the catalysts of this invention exhibit far superior performances to a known similar catalyst.

EXAMPLE 11

As second-stage oxidation catalysts, the following catalysts A to F containing at least (1) phosphorus, (2) molybdenum and (3) R (R represents at least one element selected from thallium, alkali metals and alkaline earth metals) were prepared in accordance with the disclosures of Japanese Patent Publications or Laid-Open Patent Publications indicated (the catalyst particle size 4 to 8 mesh).

A: $Mo_{12}P_2V_1Sr_1$ catalyst described in Example 1 of Japanese Patent Publication No. 31327/77

B: $Mo_{12}P_2V_1Cs_2$ catalyst described in Example 1 of Japanese Laid-Open Patent Publication No. 82013/75

C: $Mo_{12}P_2Cr_{1.5}Rb_2V_{0.1}$ catalyst described in Example 1 of Japanese Laid-Open Patent Publication 123616/75

D: $Mo_1P_{0.08}Tl_{0.16}Si_{0.08}$ catalyst (calcined at 450° C.) described in Example 3 of Japanese Patent Publication No. 24288/75

E: $Mo_1P_{0.08}K_{0.16}Ge_{0.08}$ catalyst described in Example 4 of Japanese Patent Publication No. 15011/76

F: $Mo_{12}P_2Ba_1Zn_{0.5}B_{0.5}$ catalyst described in Example 2 of Japanese Laid-Open Patent Publication No. 84519/75.

Using the catalyst used in Example 1 as a firststage oxidation catalyst, and each of the catalysts A to F as a second-stage oxidataon catalyst, the continuous first stagesecond stage method was performed in the same way as in Example 1. The results are shown in Table 2.

For comparison, the same continuous first stagesecond stage reaction was performed using the comparative catalyst used in Example 8. The results are shown in Table 2.

As a control, instead of the first-stage oxidatiaon reaction gas, a gaseous mixture of methacrolein (purity 99.5% by weight):$O_2$:$N_2$:$H_2O$=1:1.5:13.0:17.5 (mole ratio) was fed at a space velocity of 2000 $hr^{-1}$ through each of the second-stage oxidation catalysts A to F. The results are also shown in Table 2.

Since the results of the first-stage oxidation reaction were the same as in Example 1 and 8, they are omitted in Table 2. Table 2 therefore gives the results of the secondstage oxidataion reaction alone. The reaction temperatures tabulated are the maximum temperatures of the catalyst layer.

TABLE 2

| | Invention | | | | Comparison | | | | Control | | | |
|---|---|---|---|---|---|---|---|---|---|---|---|---|
| | | | MAA (based on MAL) | | | | MAA (based on MAL) | | | | MAA (based on MAL) | |
| Second-stage oxidation catalyst | Reaction temperature (°C.) | Conversion of MAL (%) | One-pass yield (%) | Selectivity (%) | Reaction temperature (°C.) | Conversion of MAL (%) | One-pass yield (%) | Selectivity (%) | Reaction temperature (°C.) | Conversion of MAL (%) | One-pass yield (%) | Selectivity (%) |
| A | 408 | 56.7 | 37.7 | 66.5 | 408 | 46.1 | 27.7 | 60.1 | 408 | 57.3 | 38.2 | 66.7 |
| B | 400 | 79.1 | 61.4 | 77.6 | 400 | 65.6 | 44.2 | 67.4 | 400 | 80.0 | 63.8 | 79.8 |
| C | 410 | 76.1 | 54.9 | 72.1 | 410 | 63.0 | 39.3 | 62.4 | 410 | 77.7 | 56.1 | 72.2 |
| D | 379 | 70.9 | 49.1 | 69.3 | 379 | 59.0 | 36.1 | 61.2 | 379 | 72.8 | 51.1 | 70.2 |
| E | 385 | 69.3 | 47.3 | 68.3 | 385 | 56.1 | 33.8 | 60.2 | 385 | 70.4 | 49.0 | 69.0 |
| F | 418 | 57.0 | 37.8 | 66.3 | 418 | 45.5 | 26.0 | 57.1 | 418 | 57.5 | 38.3 | 66.6 |

The results of Table 2 demonstrate that when the catalyst of the invention is used as a first-stage oxidation catalyst in the continuous first stage-second stage reaction, the results are much the same as in the control in which purified methacrolein is used. On the other hand, the use of the comparative catalyst not containing Pb as a first-stage oxidation catalyst gives far inferior results compared to those in the control.

EXAMPLES 12 to 14

The continuous first stage-second stage methods shown in Examples 1 to 8 were continued respectively for 1000 hours while maintaining the reaction conditions constant. Changes in the results of the reaction were examined (Examples 12 and 13). The results are shown in Table 3.

As a control, the second-stage oxidation reaction shown in Example 10 was continued for 1000 hours while maintaining the reaction conditions constant. Changes in the results of the reaction were examined (Example 14). The results are also shown in Table 3. The reaction temperatures in Table 3 show the temperatures of the metal baths.

TABLE 3

| Example | | | 12 | | 13 | | 14 | |
|---|---|---|---|---|---|---|---|---|
| Composition (atomic ratio) of catalyst | | | $Mo_{12}Bi_1Fe_{12}Co_4Ni_1Pb_1P_{0.5}K_1$ | | $Mo_{12}Bi_1Fe_{12}Co_4Ni_1P_{0.5}K_1$ | | — | |
| Reaction time which elapsed (hrs) | | | 0* | 1000 | 0* | 1000 | 0* | 1000 |
| Results of the first-stage oxidation | | Reaction temperature (°C.) | 340 | 340 | 340 | 340 | — | — |
| | i-B conversion | | 98.4 | 98.5 | 95.5 | 94.0 | — | — |
| | Proportion of unsaturated hydrocarbons formed (%) | | 2.7 | 2.6 | 7.3 | 8.5 | — | — |
| | MAL | One-pass yield (%) | 76.4 | 76.5 | 69.4 | 68.1 | — | — |
| | | Selectivity (%) | 77.6 | 77.7 | 72.7 | 72.4 | — | — |
| Results of the second-stage oxidation | | Reaction temperature (°C.) | 335 | 335 | 335 | 335 | 335 | 335 |
| | | MAL conversion (%) | 78.9 | 79.0 | 65.4 | 54.8 | 81.1 | 80.9 |
| | MAA (based on MAL) | One-pass yield (%) | 60.8 | 60.8 | 44.5 | 33.5 | 62.8 | 62.8 |
| | | Selectivity (%) | 77.1 | 77.0 | 68.0 | 61.1 | 77.4 | 77.6 |
| | Conversion of unsaturated hydrocarbons (%) | | 100 | 100 | 100 | 100 | — | — |
| | One-pass yield (%) of MAA (based on i-B) | | 46.5 | 46.5 | 30.9 | 22.8 | — | — |

*The symbol (*) denotes the early stage of reaction.

It is seen from the results of Table 3 that the catalyst of this invention gives high conversions and selectivities in the first-stage oxidation, and is suitable as a catalyst for a continuous first stage-second stage oxidation method. The comparative catalyst has poor performance in the first-stage oxidation and induces the production of large amounts of by-product unsaturated hydrocarbons, and for this reason, in the continuous first stage-second stage method using such a catalyst in the first stage, the lifetime of the second-stage oxidation catalyst decreases.

What we claim is:

1. A process for preparing methacrolein which comprises oxidizing isobutylene with molecular oxygen in the vapor phase at a temperature of 250° to 700° C. in the presence of a catalyst which has a composition of the formula $$Mo_aBi_bFe_cCo_dNi_eP_fPb_gX_hO_i$$

wherein X is at least one alkali metal element selected from the group consisting of K, Rb and Cs; a, b, c, d, e, f, g and h respectively represent the number of Mo, Bi, Fe, Co, Ni, P, Pb and X atoms, and a is 12, b is 0.1-10, c is 9-20, d is 0-12, e is 0-12 with the proviso that the sum of d and e is 0.5-15, f is 0.1-5, g is 0.05-8 and h is 0.01-5; and i is the number of oxygen atoms which satisfies the atomic valences of the other elements.

2. The process of claim 1 wherein a is 12, b is 0.5-7, c is 10-15, d is 0-10, e is 0-10 with the proviso that the sum of d and e is 0.5-12, f is 0.1-4, g is 0.1-4 and h is 0.01-4.

3. The process of claim 1 wherein R is K.

4. The process of claim 1 wherein R is Rb.

5. The process of claim 1 wherein R is Cs.

6. The process of claim 1 wherein air is used as a source of oxygen.

7. The process of claim 1 wherein the reaction is carried out in the presence of an inert gas.

8. The process of claim 1 wherein the reaction is carried out at a temperature of 250° to 550° C.

* * * * *